US006632653B1

(12) United States Patent
Astle

(10) Patent No.: US 6,632,653 B1
(45) Date of Patent: Oct. 14, 2003

(54) CONTINUOUS POLYMERASE CHAIN REACTION APPARATUS WITH MULTIPLE TEMPERATURE STATIONS

(76) Inventor: Thomas W. Astle, 607 Harborview Rd., Orange, CT (US) 06477

( * ) Notice: Subject to any disclaimer, the term of this patent is extended or adjusted under 35 U.S.C. 154(b) by 0 days.

(21) Appl. No.: 09/460,107

(22) Filed: Dec. 13, 1999

Related U.S. Application Data

(63) Continuation-in-part of application No. 09/425,070, filed on Mar. 22, 1999, now Pat. No. 6,537,752, which is a continuation-in-part of application No. 09/198,018, filed on Nov. 23, 1998.
(60) Provisional application No. 60/095,497, filed on Aug. 6, 1998, provisional application No. 60/073,329, filed on Feb. 2, 1998, and provisional application No. 60/067,895, filed on Dec. 8, 1997.

(51) Int. Cl.[7] ............................ C12M 1/34; C12M 1/00; C12Q 1/68; C12P 19/34; G01N 15/06
(52) U.S. Cl. ...................... 435/287.2; 435/6; 435/91.1; 435/91.2; 435/283; 435/287.1; 422/68.1
(58) Field of Search ........................... 435/6, 91.1, 91.2, 435/91.5, 183, 283.1, 287.1, 287.2, 288.4; 436/94; 536/23.1, 24.3, 24.33, 25.3; 422/50, 68.1, 82.07, 82.08

(56) References Cited

U.S. PATENT DOCUMENTS

| | | | | |
|---|---|---|---|---|
| 5,508,197 A | * | 4/1996 | Hansen et al. | 435/285.1 |
| 5,545,528 A | * | 8/1996 | Mitsuhashi et al. | 435/6 |
| 6,054,263 A | * | 4/2000 | Danssaert et al. | 435/4 |

OTHER PUBLICATIONS

Staatagene Catalog (1994), pp. 256 and 257. Published by Stratagene Cloning Systems, 11011 North Torrey pines Road, LA Jolla, CA 92037.*

* cited by examiner

Primary Examiner—Ethan Whisenant
Assistant Examiner—Frank Lu
(74) Attorney, Agent, or Firm—John H. Crozier

(57) ABSTRACT

In a preferred embodiment, a method of performing a reagent protocol using polymerase chain reaction, including: indexing patterns of reagent wells on a continuous basis through at least one step of reagent addition to the reagent wells; and then indexing the patterns of reagent wells on a continuous basis through a plurality of individual heat transfer stations, whereby at each of the individual heat transfer stations, the patterns of reagent wells are subjected to a unique temperature change to cause one amplification step, with the plurality of individual heat transfer stations providing total amplification required for the protocol.

4 Claims, 4 Drawing Sheets

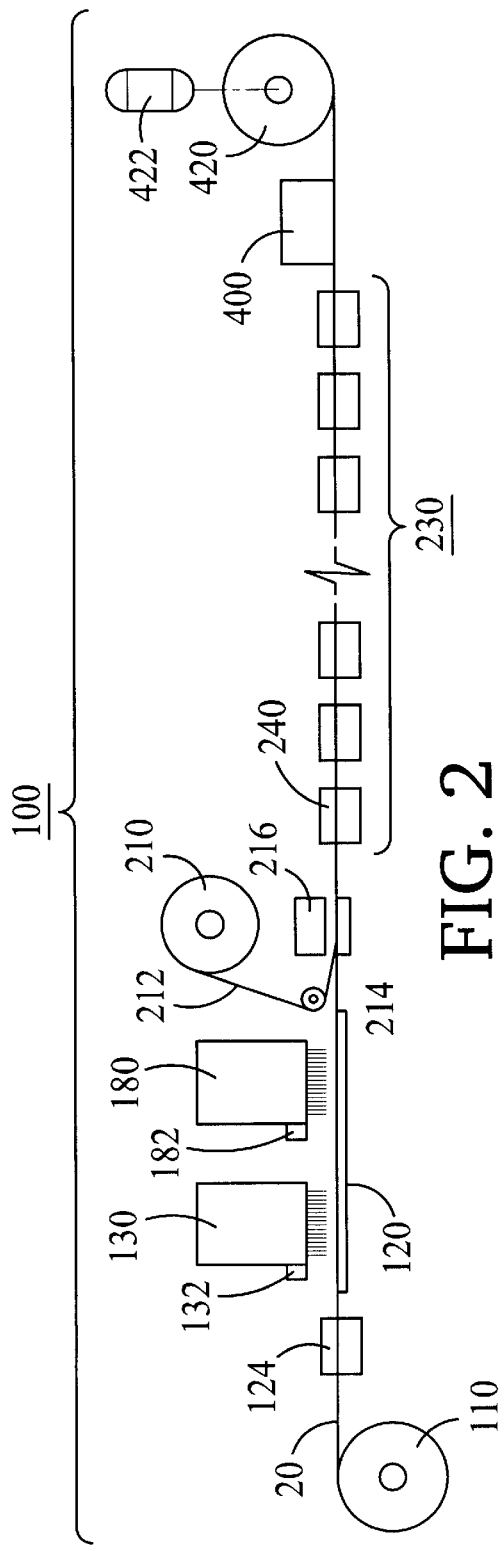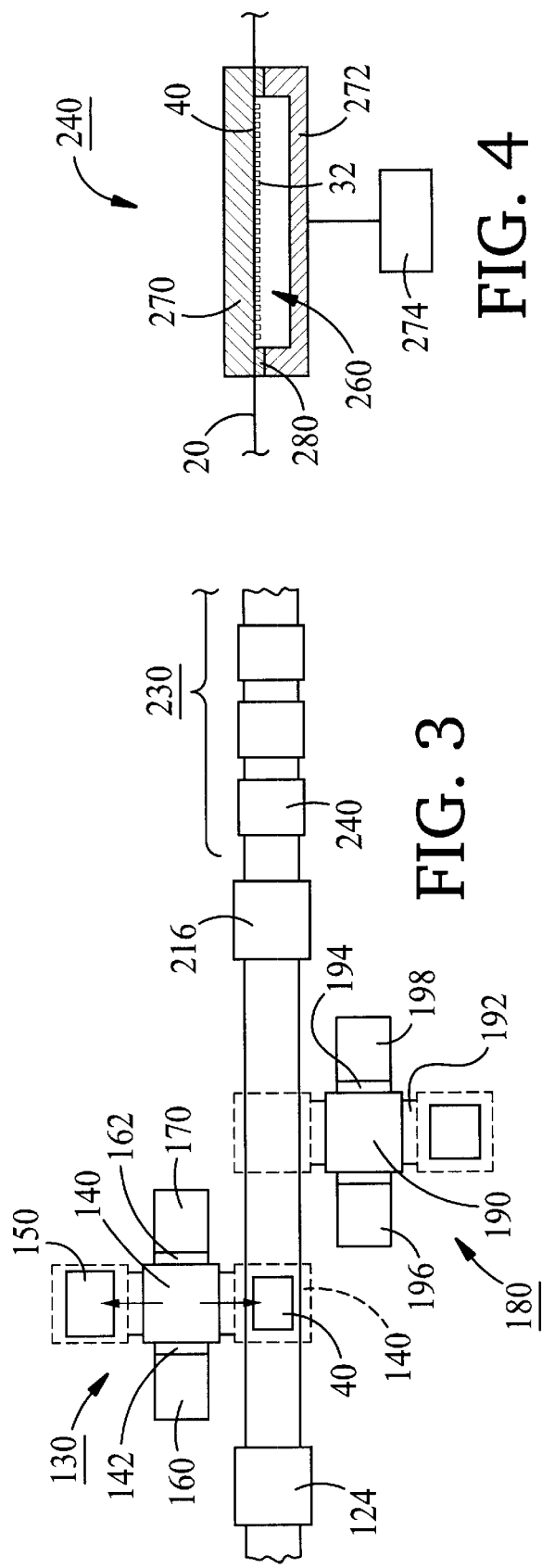

CONTINUOUS POLYMERASE CHAIN REACTION APPARATUS WITH MULTIPLE TEMPERATURE STATIONS

CROSS-REFERENCE TO RELATED APPLICATIONS

The present application is a continuation-in-part of co-pending application Ser. No. 09/425,070, filed Mar. 22, 1999, and titled TEMPERATURE CONTROL SYSTEM FOR POLYMERASE CHAIN REACTION, now U.S. Pat. No. 6,537,752, which is a continuation-in-part of application Ser. No. 09/198,018, filed Nov. 23, 1998, and titled ULTRA HIGH THROUGHPUT BIOASSAY SCREENING SYSTEM, which application claims the benefit of the filing dates of Provisional Patent Applications Nos. 60/067,895, filed Dec. 8, 1997, and titled ULTRA HIGH THROUGHPUT BIOASSAY SCREENING SYSTEM AND METHOD; 60/073,329, filed Feb. 2, 1998, and titled ULTRAHIGH THROUGHPUT BIOASSAY SYSTEM AND METHOD; and 60/095,497, filed Aug. 6, 1998, and titled USE OF CONTINUOUS CARRIER TAPE FOR POLYMERASE CHAIN REACTIONS, the disclosures of all which applications are incorporated by reference hereinto.

BACKGROUND OF THE INVENTION

1. Field of the Invention

The present invention relates to polymerase chain reactions generally and, more particularly, but not by way of limitation, to a novel continuous polymerase chain reaction process having multiple temperature stations.

2. Background Art

In the field of genomics, and other disciplines using molecular biology, the polymerase chain reaction (PCR) protocol is essential. It is an amplification technique that utilizes three basic temperatures to amplify DNA. In such a protocol, the DNA is first brought to 96° Centigrade to denature the DNA, causing it to "unwind" from the standard double helix to single strands. The denaturing process requires exposure to 96° Centigrade for approximately 15 seconds.

Next in the protocol, the DNA is exposed to a temperature of 50–55° Centigrade to anneal the single strands, normally in the presence of defined primers. Again, approximately only 15 seconds at 50–55° Centigrade is required for annealing. The next temperature is 72° Centigrade. At this extension temperature, the two single strands form two double stranded helixes, thus resulting in a two-fold amplification. The extension temperature of 72° Centigrade is only required for 30 seconds.

The foregoing temperature cycling doubles the amount of DNA on each cycle. After 25 to 35 cycles, non-measurable quantities of DNA now become readily detectable because of the power of PCR and its exponential amplification.

The current state-of-the-art techniques for thermocycling comprise two basic methods. One is a batch method, whereby a group of PCR reaction plates is physically moved from one water temperature bath to another. The second, and more popular, method is the use of thermocycling instrumentation using Peltier thermoelectric devices to change the temperature of an individual PCR plate.

The Peltier thermoelectric device is clean and efficient; however, it process only one plate at a time. While the latter feature is an advantage for small operators, it is a disadvantage in high volume operations. High volume laboratories will have bench tops with many thermocyclers side by side. At a cost of $5,000–6,000 each, a considerable investment is required, particularly since the nature of genomic testing requires a high volume of testing.

Another disadvantage of the thermocycling instrument is the time required to move from one temperature to the next. At present, the popular Peltier devices can only change temperature at a rate of about 3 Centigrade degrees per second. The change from 96° Centigrade to 50° Centigrade requires 15 seconds transient time plus the 15 seconds at the annealing temperature. From 50° Centigrade to 72° Centigrade requires 7 seconds transient time plus the 30 second extension time. From 72° Centigrade to 96° Centigrade requires 8 seconds. Thus, for the 60 seconds of protocol time, an additional 30 seconds is required for transient time. This adds 50 percent to the overall time cycle. While insignificant on a single cycle, the time is an additional 12 minutes per plate on a 25 cycle protocol and 17 minutes per plate on a 35 cycle protocol.

The batch method of inserting a stack of plates into separate water baths decreases the temperature transient time. While the batch method is suitable for batches of large numbers of plates, the set up and handling time makes running small batches less attractive.

Accordingly, it is a principal object of the present invention to provide a PCR process that greatly reduces temperature transient times.

It is a further object of the invention to provide such a process that is economical for either a small or a large number of DNA samples.

It is another object of the invention to provide such a process that is easily implemented.

A further object of the invention is to provide such a process that is continuous.

Other objects of the present invention, as well as particular features, elements, and advantages thereof, will be elucidated in, or be apparent from, the following description and the accompanying drawing figures.

SUMMARY OF THE INVENTION

The present invention achieves the above objects, among others, by providing, in a preferred embodiment, a method of performing a reagent protocol using polymerase chain reaction, comprising: indexing patterns of reagent wells on a continuous basis through at least one step of reagent addition to said reagent wells; and then indexing said patterns of reagent wells on a continuous basis through a plurality of individual heat transfer stations, whereby at each of said individual heat transfer stations, said patterns of reagent wells are subjected to a unique temperature change to cause one amplification step, with said plurality of individual heat transfer stations providing total amplification required for said protocol.

BRIEF DESCRIPTION OF THE DRAWING

Understanding of the present invention and the various aspects thereof will be facilitated by reference to the accompanying drawing figures, submitted for purposes of illustration only and not intended to define the scope of the invention, on which:

FIG. 2 is a fragmentary, schematic side elevational view of a continuous PCR processing line according to the present invention.

FIG. 3 is a fragmentary, top plan view of pipettor heads servicing the processing line of FIG. 1.

FIG. 4 is a fragmentary, side elevational view of a heat exchanger used in the present invention.

DETAILED DESCRIPTION OF THE PREFERRED EMBODIMENTS

Figure 1:
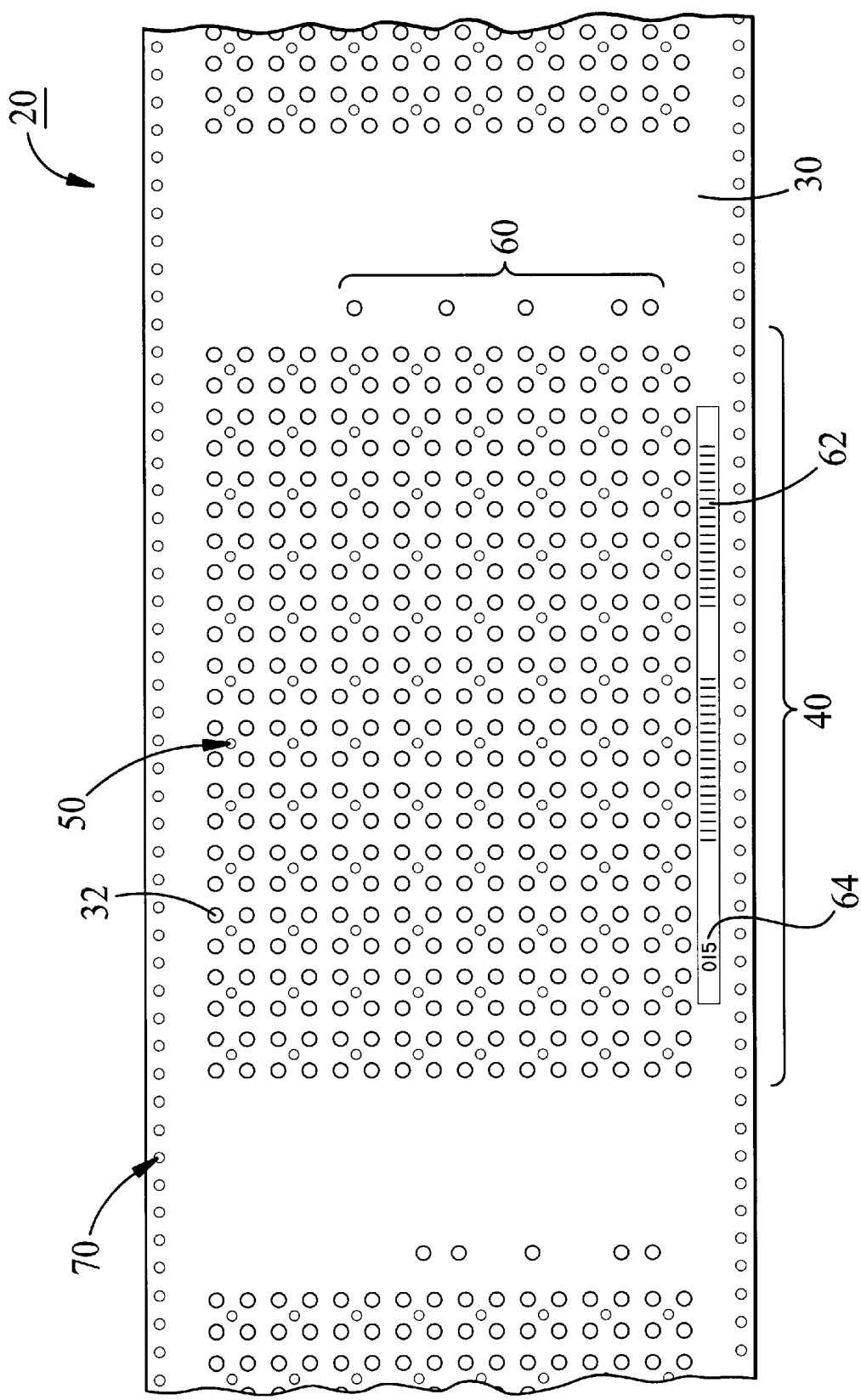
FIG. 1 is a fragmentary, top plan view of a carrier tape used in the present invention.

Reference should now be made to the drawing figures, on which similar or identical elements are given consistent identifying numerals throughout the various figures thereof, and on which parenthetical references to figure numbers direct the reader to the view(s) on which the element(s) being described is (are) best seen, although the element(s) may be seen also on other views.

FIG. 1 illustrates a sprocket-driven, multi-well carrier tape, generally indicated by the reference numeral 20. The above-referenced applications describe, in further detail, carrier tape 20 and uses thereof.

Carrier tape 20 includes a substrate web 30 in which is formed a plurality of 10-microliter reagent wells, as at 32, embossed into the web, or thermoformed in the web, in patterns of 16×24 matrixes, with the wells on 4.5 mm centers. Such a pattern is indicated by the reference numeral 40. A plurality of vent holes, as at 50, may be provided through substrate web 30 to assist in effecting a seal between the substrate web and a seal layer (not shown on FIG. 1) when a seal layer is used. A series of holes comprising a binary code of identification, such as holes 60, may be formed through substrate web 30 in order to identify pattern 40. Alternatively, or in addition, a bar code 62 and/or humanly readable indicia 64 may be provided for pattern identification. Other suitable identifying indicia may be provided as well. Precision sprocket holes, as at 70, are provided spaced along either edge of carrier tape 20 to provide a means of transporting patterns 40 from one location to the next within a processing line. This enables a positive, position-controlled, indexing drive system. The drive system may, for example, be walking beams, geneva motions, electronic stepper drives, or pneumatic indexing mechanisms.

Carrier tape 20 may be constructed of one of several thermoplastic materials. Polypropylene is a satisfactory choice where there is no requirement that the material be clear. Where clearness is a requirement, polycarbonate provides a suitable clear material that facilitates optical readout of the final test results. Pattern 40 of 384 wells is a common format used in biotechnology.

Carrier tape 20 starts with a thickness of 20 mils. When wells 32 are formed, the wall thickness of each well decreases to a thickness of approximately 2 mils. This thin wall around the contents of a well provides a minimal thermal barrier to heat transfer.

FIG. 2 illustrates a PCR processing line, generally indicated by the reference numeral 100. Processing line 100 includes a payoff reel 110 that supplies virgin carrier tape 20 (FIG. 1) to the processing line. An intermittent motion indexing drive 120 engages sprocket drive holes 70 (FIG. 1) and advances carrier tape 20 precisely one carrier tape pattern 40. The indexing motion can be derived one of several ways. If can be stepper motor, cam drive, walking beam, geneva motions, or reciprocating air cylinders. In addition to indexing carrier tape 20 forward, indexing mechanism 120 clamps the carrier tape to the indexing mechanism so as to provide a positive position controlled drive system.

A punch mechanism 124 punches 8-bit binary code 60 (FIG. 1) between patterns. Binary code 60 provides a positive sample identification system. This code can be read at subsequent stations, or processing equipment, by contact fingers, air pressure jets, or photometric means. Punch mechanism 124 may alternatively, or in addition, include a bar code printer.

With reference primarily to FIG. 3, carrier tape 20 is next indexed such that pattern 40 (FIG. 1) is moved under a first transfer station, generally indicated by the reference numeral 130. First transfer station 130 includes an identifying indicia reader 132 and a 384-well pipettor head 140 mounted on a Y-axis traverse 142 to allow the pipettor head to aspirate or dispense at either of the positions shown in solid or broken lines. Y-axis traverse 142 also permits pipettor head 140 to move to tip washing station 150. A separate Z-axis traverse (not shown) built into pipettor head 140 allows vertical motion to reach three stations. An infeed plate stacker 160 can feed sample trays in the 384-well format (not shown) down onto an X-axis traverse 162 which can move the plate for access by pipettor head 140. Following that, X-axis traverse 162 can then transport the plate to an output plate stacker 170.

A typical operating sequence would be to move a 384-well microplate from infeed stacker 160 down to X-axis traverse that would transport the microplate to pipettor head 140. Pipettor head 140 (solid position) would then aspirate 384 aliquots from the microplate and dispense (broken lines) the 384 samples onto pattern 40. Pipettor head 140 would then traverse to tip washing station 150 to wash the tips (not shown) of the pipettor head. Concurrently with the later motion, X-axis traverse 162 would move the used microplate to outfeed stacker 170 and retrieve the next microplate from infeed stacker 160. The cycle sequence would then repeat for the next indexed pattern on carrier tape 20.

Continuing to refer primarily to FIG. 3, following first transfer station 130 is a second transfer station generally indicated by the reference numeral 180. Second transfer station 180 is identical to first transfer station 130 and includes an identifying indicia reader 182 and a 384-well pipettor head 190, Y-axis and X-axis traverses 192 and 194, respectively, an infeed stacker 196, and an outfeed stacker 198.

Referring now again primarily to FIG. 2, in a typical operation, DNA samples would be added to carrier tape 20 at first transfer station 130 and primer/master mix would be added to the carrier tape at second transfer station 180.

Binary code and/or bar code readers 132 and 182 at, respectively, first and second transfer stations 130 and 180 read the identification of incoming microplate samples. These numbers are tied to the carrier tape pattern number in a database to maintain a sample audit trail.

Continuing to refer to FIG. 2, following the addition of all reagents, carrier tape 20 is sealed. A payoff reel 210 contains a heat seal top covering 212 which is paid out over an idler roller 214 and heat sealed to carrier tape 20 at sealing station 216. At sealing station 216, a heat seal head closes, sealing top covering 212 to carrier tape 20.

As indicated on FIG. 2, carrier tape 20 is now indexed through the PCR section of processing line 100, the PCR section being indicated generally by the reference numeral 230. PCR section 230 consists of a plurality of identical thermal transfer stations, as at 240, with each station providing one set of temperature changes to the reagents in the pattern, resulting in one amplification cycle for the reagents. The number of thermal transfer stations 240 provided is dependent on how many PCR cycles are required and, ordinarily, there are at least as many individual thermal transfer stations as there are amplification cycles required by the protocol. This requires enough thermal transfer stations in processing line 100 to handle the maximum number of amplification cycles for which the processing line is designed. A typical processing line 100 may have 35 or more thermal transfer stations 240, although all thermal transfer stations may not be used for all protocols. If 35 thermal transfer stations 240 are provided and a particular protocol requires only 25 PCR cycles, then the remaining 10 thermal transfer stations would not be activated. The unused thermal transfer stations 240 do not temperature cycle and in essence are bypassed, although carrier tape 20 will index through them.

Referring to FIG. 4, thermal transfer station 240 includes a small liquid chamber 260 that is clamped to the bottom side of carrier tape 20 around pattern 40 (FIG. 1). Chamber 260 is created between a backup plate 270 and a heat exchange reservoir 272. This clamping motion may be provided by one of several means for each thermal transfer station 240, such as an air cylinder 274, or it may be a common mechanical motion, clamping all thermal transfer stations in common. An elastomeric gasket 280 effects a liquid tight seal between the upper edges of heat exchange reservoir 272 and the bottom of carrier tape 20. The heat transfer medium in heat exchange reservoir 272 is in direct contact with reagent wells 32 protruding from the bottom of carrier tape 20. Thus, the heat transfer is by intimate conduction. This, combined with the thin walls of reagent wells 32, provides a very fast heat transfer to the PCR components within the wells.

Backup plate 270 and heat exchange reservoir 272 are fabricated from a heat insulating material such as polypropylene to minimize the heat loss through conduction by these elements on the quick changing liquid temperature within each heat transfer station 240.

Figure 5:
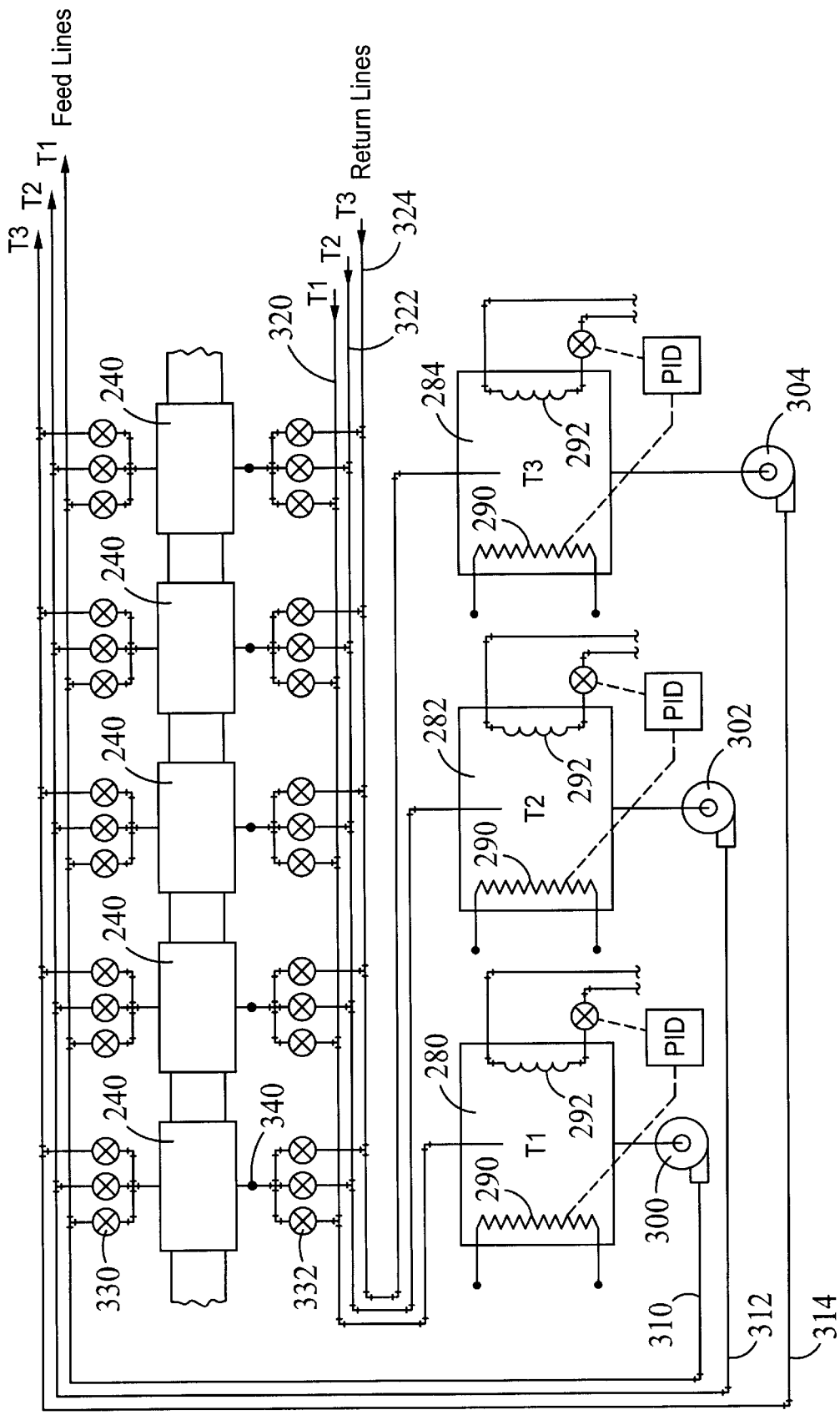
FIG. 5 a flow diagram of the temperature control system of the present invention.

FIG. 5 illustrates the temperature control system for thermal transfer stations 240 and includes, in the system shown, three reservoirs 280, 282, and 284 which may contain water, for example, as the heat transfer medium. For the protocol described above, reservoir 280 would contain water at the denaturing temperature of 95° Centigrade ("T1"), reservoir 282 would contain water at the annealing temperature of 55° Centigrade ("T2"), and reservoir 284 would contain water at the extension temperature of 72° Centigrade ("T3"). Each of reservoirs 280, 282, and 284 has a heating element 290, a cooling coil 292, and a proportional/integral/derivative controller 294, the latter being able to cycle between heating and cooling to hold precise temperatures within the reservoirs.

Water from reservoirs 280, 282, and 284 is fed to thermal transfer stations 240 by means of, respectively, circulating pumps 300, 302, and 304 through feed lines 310, 312, and 314 and is returned to the reservoirs, respectively, through return lines 320, 322, and 324.

Each heat transfer station 240 has its own series of feed and return solenoid valves, as at, respectively, 330 and 332. When the program requires, the extension temperature T1, valves 330 and 332 open and water at temperature T1 flows through heat transfer station 240, effecting heat transfer to the reagents contained in wells 32 (FIG. 4). When a fast response temperature sensor 340 located in the return from heat transfer station 240 reaches a predetermined temperature, it initiates the timing sequence for that temperature at that heat transfer station. When the time for T1 expires, the feed and return valves for T1 close and the feed and return valves for T2 open. This sequence is repeated for T3. When the T3 cycle time expires, the feed valve closes, but the return valve stays open, allowing some drainage from the heat transfer station.

When all heat transfer stations 240 have completed their temperature cycles, the heat transfer stations are opened enough to allow carrier tape 20 to index one station. The entire sequence then repeats for the next index. Each index equates with a change of temperature through T1, T2, and T3 for each station. These amplification cycles occur simultaneously at all heat transfer stations 240 being used in the protocol. After the first pattern 40 has progressed through all heat transfer stations 240, a completed pattern of reagents is presented on each indexing of the system. Thus, if the index rate is one index every 1.5 minutes, a complete set of samples will be completed thereafter every 1.5 minutes.

Reference should be made again to FIG. 2. Following the amplification by PCR, there are several options for post processing. As shown on FIG. 2, the processed carrier tape 20 may be indexed directly into a fluorescent reader 400. In this case, the reading is made without removing seal layer 212. A transparent seal material is used for seal layer 212 and the reading of the well contents is made through the seal layer. As carrier tape 20 exits reader 400, it may be wound on a take up reel 420 driven by a torque motor 422. Another option is to cut carrier tape 20 into pieces for disposal in a container (not shown).

Figure 6:
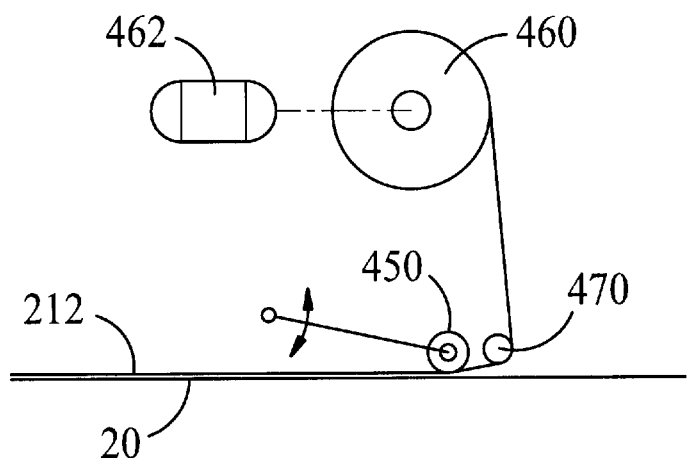
FIG. 6 is a fragmentary, side elevational view of the mechanism for removal of a heat seal material.

While a heat seal material provides a more secure seal, the use thereof does require additional complexity for its removal, as is shown on FIG. 6. Seal layer 212 is a peelable seal material bonded to carrier tape 20 by means similar to that used for lids in the food industry. At the time of forward index motion of carrier tape 20, a heated roll 450 is brought into contact with the top of seal layer 212. This provides a line of high temperature across seal layer 212 which, at the point of contact, softens the seal layer. Tension is applied to seal layer 212 by take up reel 460 driven by torque motor 462. This separates seal layer 212 from carrier tape 20 and draws the seal layer over guide roller 470 and winds the seal layer upon take up reel 460. When the forward index motion of carrier tape 20 stops, heated roll 450 swings away from contact, so as not to burn through when the carrier tape is stopped. Removal of seal layer 212 permits access to the contents of reagent wells 32 (FIG. 1). The contents of wells 32 can then be aspirated by another pipettor station and transferred to another element for further use or processing.

Some applications may not require sealing the top of carrier tape 20 and the clamping action at individual heat transfer stations 240 (FIG. 2) may be sufficient to prevent evaporation and cross contamination.

Figure 7:
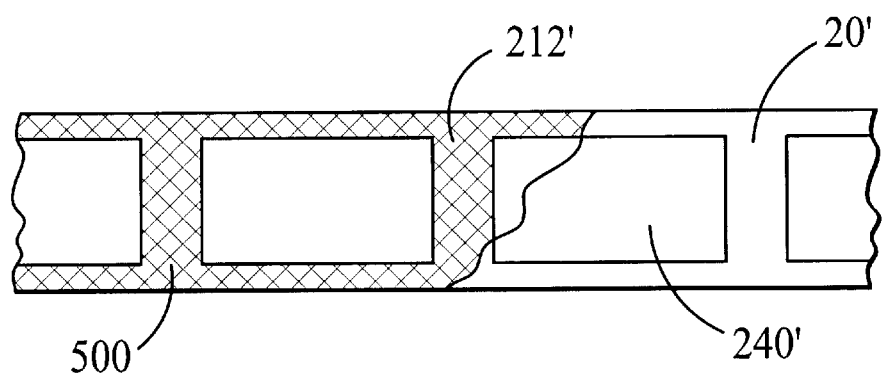
FIG. 7 is a top plan view, partially cut-away, illustrating an alternative embodiment of sealing carrier tape used in the present invention.

Referring to FIG. 7, another alternative is to use a seal layer 212' on a carrier tape 20', the seal layer having a printed pressure sensitive adhesive pattern 500 that would only bond around the perimeter of well patterns 240'. The area of seal layer 212' over well patterns 240' would not have adhesive. This arrangement facilitates removal of seal layer 212' and eliminates any cross contamination between well patterns 240'. Clamping pressure at each heat transfer station 240 prevents cross contamination between wells 32 (FIG. 1) within well patterns 240'.

Figure 8:
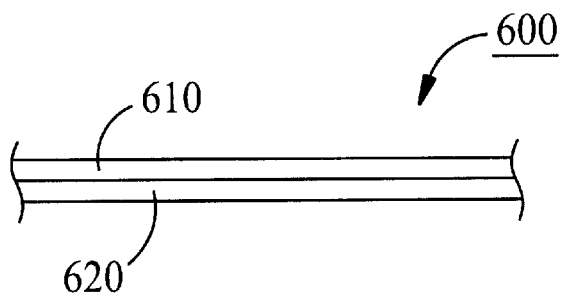
FIG. 8 is an enlarged, fragmentary, side elevational view, of a heat seal useful in the present invention.

FIG. 8 illustrates a heat seal layer, generally indicated by the reference numeral 600. Heat seal layer 600 provides a more secure sealing method and consists of a two part construction comprising a top layer 610 with high melting point and strength bonded to a low temperature sealing layer 620. A typical heat seal layer 600 would be a bifilm combination of polyester/ethylene vinyl acetate or of an aluminum foil with a heat seal coating. The heat seal material or coating would bond to the carrier tape, creating a liquid tight seal around the perimeter of each individual reagent well.

In the embodiments of the present invention described above, it will be recognized that individual elements and/or features thereof are not necessarily limited to a particular embodiment but, where applicable, are interchangeable and can be used in any selected embodiment even though such may not be specifically shown.

Terms such as "upper", "lower", "inner", "outer", "inwardly", "outwardly", and the like, when used herein, refer to the positions of the respective elements shown on the accompanying drawing figures and the present invention is not necessarily limited to such positions.

It will thus be seen that the objects set forth above, among those elucidated in, or made apparent from, the preceding description, are efficiently attained and, since certain changes may be made in the above construction and/or method without departing from the scope of the invention, it is intended that all matter contained in the above description or shown on the accompanying drawing figures shall be interpreted as illustrative only and not in a limiting sense.

It is also to be understood that the following claims are intended to cover all of the generic and specific features of the invention herein described and all statements of the scope of the invention which, as a matter of language, might be said to fall therebetween.

I claim:

1. An apparatus for performing a reagent protocol using polymerase chain reaction, comprising:
   (a) means to index patterns of reagent wells on a continuous basis through at least one step of reagent addition to said reagent wells;
   (b) means to index said patterns of reagent wells on a continuous basis through a plurality of individual heat transfer stations, whereby at each of said individual heat transfer stations, said patterns of reagent wells are subjected to a unique temperature change to cause one amplification step, with said plurality of individual heat transfer stations providing total amplification required for said protocol; and
   (c) means to seal said reagent wells following said at least one step of reagent addition to said wells, wherein said patterns of reagent wells are sealed to provide a liquid tight but peelable seal as provided by pressure sensitive adhesive or heat seal methods.

2. An apparatus for performing a reagent protocol using polymerase chain reaction, comprising:
   (a) means to index patterns of reagent wells on a continuous basis through at least one step of reagent addition to said reagent wells;
   (b) means to index said patterns of reagent wells on a continuous basis through a plurality of individual heat transfer stations, whereby at each of said individual heat transfer stations, said patterns of reagent wells are subjected to a unique temperature change to cause one amplification step, with said plurality of individual heat transfer stations providing total amplification required for said protocol;
   (c) means to seal said reagent wells following said at least one step of reagent addition to said wells; and
   (d) separate heat exchanger compartments are clamped to a lower surface of a thermoplastic web containing said patterns of reagent wells to form a liquid tight seal around individual said patterns of reagent wells.

3. An apparatus, as defined in claim 2, further comprising: means to cause heat exchange fluid to flow through each of said separate heat exchanger compartments for specific time controlled periods.

4. An apparatus for performing a reagent protocol using polymerase chain reaction, comprising:
   (a) means to index patterns of reagent wells on a continuous basis through at least one step of reagent addition to said reagent wells;
   (b) means to index said patterns of reagent wells on a continuous basis through a plurality of individual heat transfer stations, whereby at each of said individual heat transfer stations, said patterns of reagent wells are subjected to a unique temperature change to cause one amplification step, with said plurality of individual heat transfer stations providing total amplification required for said protocol;
   (c) means to seal said reagent wells following said at least one step of reagent addition to said wells; and
   (d) means to peel sealing material from a top of said thermoplastic web to provide access to said reagents by a single or multiple well pipettor, said means to peel including a heated pressure roller in contact with said sealing material to apply a line of heat across said thermoplastic web to soften bonding of said sealing material to said thermoplastic web to permit ease of removal by applying tension to said sealing material.

* * * * *